United States Patent

Hoffmann et al.

[11] Patent Number: 6,069,261
[45] Date of Patent: May 30, 2000

[54] METHOD OF CHEMICALLY REACTING SUBSTANCES IN A REACTION COLUMN

[75] Inventors: Ulrich Hoffmann, Northeim; Ulrich Kunz, Clausthal-Zellerfeld, both of Germany

[73] Assignee: RWE-DEA Aktiengesellschaft für Mineraloel und Chemie, Germany

[21] Appl. No.: 09/068,177
[22] PCT Filed: Oct. 26, 1996
[86] PCT No.: PCT/DE96/02056
§ 371 Date: May 4, 1998
§ 102(e) Date: May 4, 1998
[87] PCT Pub. No.: WO97/16243
PCT Pub. Date: May 9, 1997

[30] Foreign Application Priority Data

Nov. 4, 1995 [DE] Germany .................. 195 41 213

[51] Int. Cl.$^7$ ................................. C07C 231/00
[52] U.S. Cl. .................. 554/69; 554/167; 554/168; 554/169; 564/133; 568/338; 568/343; 568/382; 568/388; 568/463
[58] Field of Search .................. 554/69, 167, 168, 554/169; 564/133; 568/338, 343, 382, 388, 463

[56] References Cited

U.S. PATENT DOCUMENTS

| 2,384,793 | 9/1945 | Bruun et al. . |
| 2,759,967 | 8/1956 | Cash et al. . |
| 3,124,526 | 3/1964 | Butler et al. . |
| 5,449,501 | 9/1995 | Luebke et al. . |

FOREIGN PATENT DOCUMENTS

| 678400 | 5/1994 | Australia . |
| 0643033 | 3/1995 | European Pat. Off. . |
| 976413 | 8/1963 | Germany . |
| 4234779 | 4/1994 | Germany . |
| WO 94/19079 | 9/1994 | WIPO . |
| 0670178 | 9/1995 | WIPO . |

OTHER PUBLICATIONS

J. Krafczyk, et al.: "Application of Catalyst Packings for the Manufacture of methyl acetate by Reactive Rectification," Chem,–Ing,–Tech. 66 (1994) Nr. 10, pp. 1372–1375.

Primary Examiner—Deborah D. Carr
Attorney, Agent, or Firm—Browning Bushman

[57] ABSTRACT

A process carried out in a reaction column for the chemical reaction of substances the reaction of which is affected by an unfavorable equilibrium position of the main reaction or a preceding equilibrium, wherein during the reaction one or more substances to be separated are continuously removed from the reaction mixture by one or more auxiliaries.

16 Claims, 1 Drawing Sheet

Reaction Stripper Operation Taking The Production Of Fatty Acid Esters From Fatty Acids And Fatty Alcohols As An Example

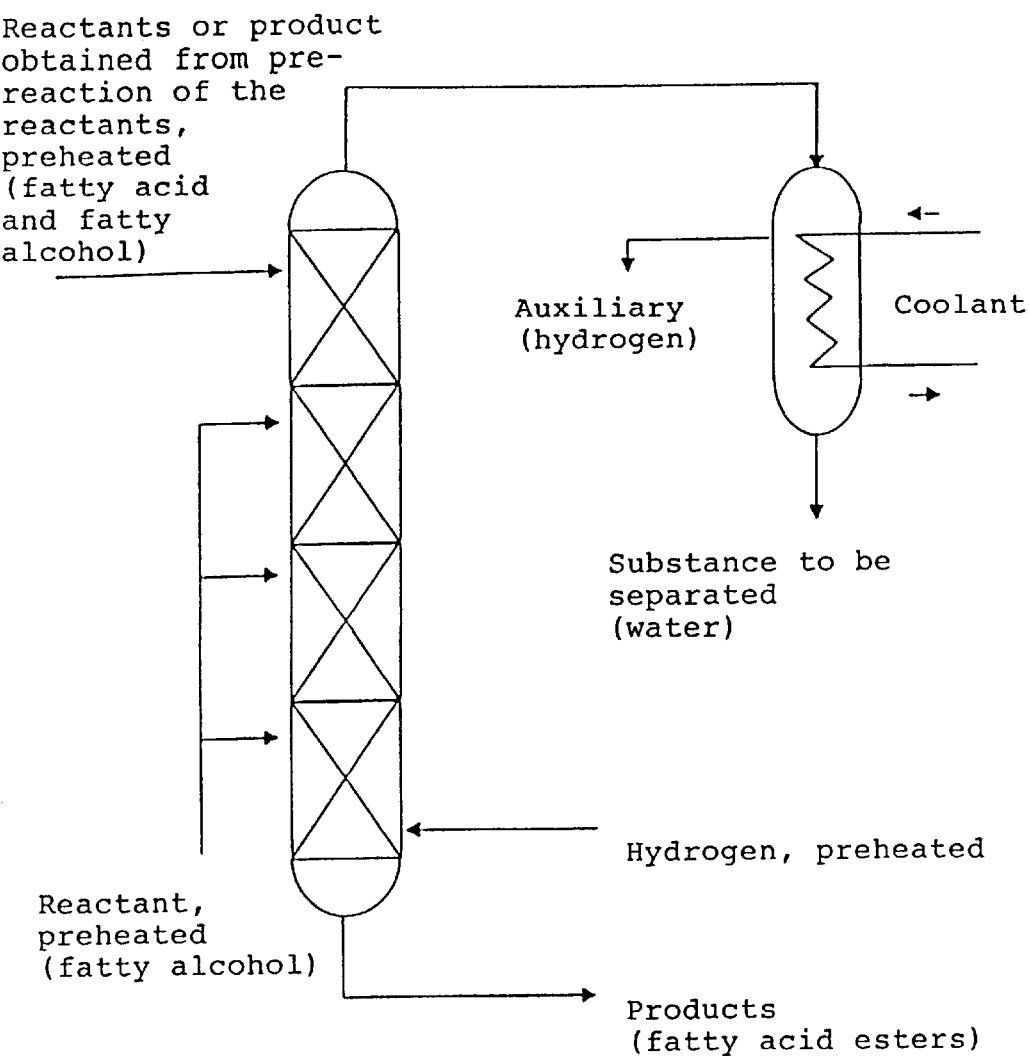
FIG. 1   Reaction Stripper Operation
Taking The Production Of Fatty Acid Esters
From Fatty Acids And Fatty Alcohols As An
Example 6,069,261

METHOD OF CHEMICALLY REACTING SUBSTANCES IN A REACTION COLUMN

This application is a 371 of PCT/DE96/02056 filed Oct. 26, 1996.

BACKGROUND OF THE INVENTION

1. Field of the Invention

The present invention relates to a process carried out in a reaction column for the chemical reaction of substances the reaction of which is affected by an unfavorable equilibrium position of the main reaction or a preceding equilibrium, wherein during the reaction one or more substances to be separated are continuously removed from the reaction mixture by one or more auxiliaries.

2. Description of the Prior Art

In the past, reactive distillation proved successful in processes wherein conversion is impaired by the position of the chemical equilibrium forming the basis for reaction. Besides the production of ethers which are used for example as antiknock additives in fuels, esterification is another field of application. Prior art processes of esterification are reactive distillation processes allowing continuous separation of the water from reaction by distillation. See e.g. J. Krafczyk and J. Gmehling, Chem. Ing. Tech., vol. 66 (1994), p. 1372; and C. Breucker, V. Jordan, M. Nitsche, and B. Gutsche, Chem. Ing. Tech., vol. 67 (1995), p. 430. During conventional reactive distillation the temperatures in the column are such that all substances, except for the bottoms, are heated to boiling point.

In the known processes, separation of the water from reaction is effected by a reactant which, in most cases, must be charged in high excess. It is therefore necessary that at the given pressure the temperature for separation be equal to or higher than the distillation temperatures of the reactants. The reactants employed in said processes are an auxiliary and an additional substance. In esterification processes the alcohol, if used in excess, is both the reactant for the esterification reaction and the auxiliary for removing the water from reaction. Furthermore, it is necessary to determine the ratio at which the reactants are used in order to achieve efficient separation. According to C. Breucker et al., separation of the water from reaction, if the reactants are present in low excess, is a challenging task for process engineers. Up to now, this problem has been tackled by using batch or cascade processes employing several reactors.

One embodiment which is well known in the art is the one-stage esterification using an entraining agent and taking advantage of azeotrope formation. See e.g. Organikum, VEB Deutscher Verlag der Wissenschaften, Berlin (1977), p. 71–73. Processes for producing esters from carboxylic acids and alcohols with continuous separation of condensed water in a column using entraining agents, such as benzene, methanol, and butyl alcohol are described in DE 976 413 B. The entraining agent used according to U.S. Pat. No. 2,384, 793 is butane.

WO 94/19079 discloses a process for producing bisphenol A from acetone and phenol while splitting off water. The resultant water from the reaction is removed using an inert stripping gas. The aforesaid process employs a reactor containing a liquid catalyst or a particulate, suspended catalyst, while the reactor itself is equipped with trays, drains, and/or hold-back screens.

BRIEF SUMMARY OF THE INVENTION

It is the object of the present invention to provide a process allowing to enhance the conversion in equilibrium reactions and, in particular, to remove a substance which has formed and must be separated in a continuous, gentle, and most effective way in a column by using an auxiliary.

It was surprisingly found that in columns with fixed-bed catalysts permanent gases are particularly suitable stripping gases serving this end. The advantageous effect of the stripping process should be utilized to support the reaction course and to prevent at the same time that a reactant is present in high stoichiometric excess. Once the auxiliary has fulfilled its task, it should be returnable to the process in a simple way. By using the present process it should be possible to avoid coupling of the process parameters, such as process temperature-pressure-distillation temperature-educts ratio, which is inherent to prior art processes.

According to the present invention, the problem is solved by a process carried out in a reaction column for the chemical reaction of substances the reaction of which is affected by an unfavorable equilibrium position of the main reaction or a preceding equilibrium, wherein during the reaction one or more substances to be separated are continuously removed from the reaction mixture by one or more auxiliaries. This is achieved by passing a stripping gas, i.e. a permanent gas or a mixture of permanent gases, as an auxiliary through the reaction column in which a solid catalyst is arranged as a fixed bed and adjusting temperature and pressure such that all the educts are present as liquids or as solutions of solids and that the substance(s) in the reaction column is (are) predominantly present in gaseous/vaporous form. The stripping gas is preferably led countercurrently to the liquid stream. Stripping and reaction take place simultaneously in the reaction column. The catalyst may be arranged as a regular packing or an irregular bulk.

DETAILED DESCRIPTION OF THE INVENTION

The continuously charged auxiliary is a permanent gas. According to the present invention, permanent gases are gases which cannot be liquefied at temperatures of greater than −30° C. Furthermore, permanent gases as defined in the present invention are gases consisting of 5 or fewer atomic molecules and mixtures thereof, including $C_1$ hydrocarbons. Particularly suitable substances are those the molecules of which consist of only one element, such as nitrogen ($N_2$) or hydrogen ($H_2$), hydrogen being particularly preferred. Said permanent gases serve as stripping gas for the product to be separated. This stripping gas differs from a conventional entraining agent in that it is already present in gaseous form, whereas the entraining agent must first be converted to a gas.

Considerable evaporation heat is required for this conversion. Moreover, it is essential that the product to be withdrawn from the equilibrium be also present in the gaseous phase. In the instant case it can partly be present as a liquid.

The process according to this invention is of advantage whenever it is impossible to heat all the reactants or products to boiling point which would result in decomposition of the products or undesired side reactions. In said cases, prior art reactive distillation processes cannot be employed because the reactants would decompose. Therefore, the instant novel process is particularly suitable whenever natural or temperature-sensitive substances are to be converted. During this conversion the continuous removal of a low-molecular reaction product has a favorable effect on the course of reactions wherein the reactants must not be heated to boiling point.

The catalyst is a fixed-bed catalyst. In a preferred embodiment the reaction column is operated as a trickle column of which about 30 to 60 vol %, preferably 50 vol % are utilized by the stripping gas as free gas space, whereas 30 to 50 vol %, preferably 40 vol % of the column is occupied by solid substance, i.e. the fixed-bed catalyst. The remaining reaction space, preferably 10 vol % or less, is occupied by the trickling liquid. Irrespective of other process parameters, high catalyst concentrations can be chosen in a wide range. In contrast to prior art processes, the ratio of catalyst:liquid phase is surprisingly high.

When using a fixed bed, the residence time of the liquid phase can be adjusted by the stripping gas velocity. The residence time of the liquid phase is high with higher velocities of the stripping gas volume. The stripping gas throughput can be adjusted in a wide range without having an adverse effect on the course of process.

The effect of the stripping gas can be modified by an additional auxiliary which is a conventional entraining agent, such as benzene, toluene, or hexane, the latter one being particularly preferred. In this case the stripping gas removes the substance to be separated together with the entraining agent which is in gaseous form under the operating conditions in the stripping column.

When using entraining agents as auxiliaries in addition to permanent gases, the amount of permanent gas in the reaction column is greater than 80 mol % of the auxiliaries charge, while the amount of entraining agent accordingly makes up to 100 mol %. The molecular portion of entraining agent is by at least the factor 4 smaller than the amount of permanent gases in the reaction column.

Reactions for which this novel process can be employed generally proceed according to the following equation:

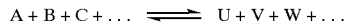

At least one of the products—the substance to be separated—can be vaporized under the reaction conditions of the reaction stripper or can be converted to vapor by the stripping gas. The reaction is an equilibrium reaction or is influenced in its course by a preceding equilibrium. The following types of reaction are given as examples:

Aldol Condensation

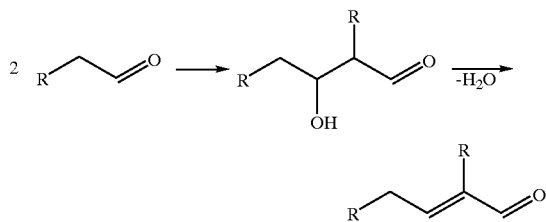

Knoevenagel Condensation

This condensation is a special case of aldol reaction followed by aldol condensation: methylene components having particularly high CH acidity, such as malonic acid, malonic semi-ester, malonic ester, cyanoacetic acid, cyanoacetic acid ester etc., are reacted with aldehydes and ketones.

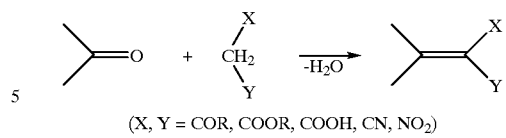

(X, Y = COR, COOR, COOH, CN, NO$_2$)

Example of a Substance

The reactants are sensitive to temperature and have higher boiling points than the auxiliary. The water to be separated (substance to be separated) is removed by the stripping gas, or the water to be separated plus an additional entraining agent, such as hexane, benzene, or toluene, hexane being the preferred entrainer, form an azeotrope in which case the permanent gas leaves the reaction stripper overhead together with entraining agent and water. The product, benzal malonic acid diethyl ester, is the highest boiling substance (186° C. at 18 torr) leaving the column at the bottom.

| Reactants | Boiling Point | Catalyst | Auxiliary |
| --- | --- | --- | --- |
| Benzaldehyde | 177° C. | Bases, e. g. basic ion exchangers, carbonates of alkali metals and alkaline earth metals | Stripping gas or stripping gas + hexane |
| Malonic acid diethyl ester | 94–96° C. at 11 torr | | |

Preparation of Enamines

Enamines are formed by reaction of aldehydes and ketones with secondary amines. This route is an important one for the formation of intermediates for organic syntheses. An important field of application is the formation of heterocycles employing appropriate reactants.

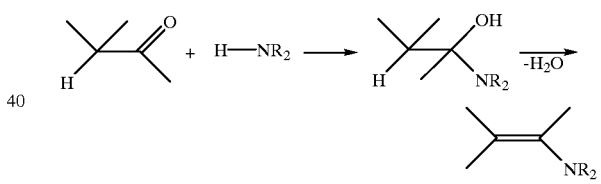

Example of a Substance

Like in the example given hereinabove, the product β-benzyl aminocrotonic acid ethyl ester is the highest boiling substance (b.p. 140° C. at 0.5 torr). The stripping gas or stripping gas plus entraining agent as an auxiliary transport the water (substance to be separated) to the top of the apparatus. The product leaves the reaction stripper at the bottom.

| Reactants | Boiling Point | Catalyst | Auxiliary |
| --- | --- | --- | --- |
| Acetoacetic acid ethyl ester | 68–79° C. at 11 torr | Acids, e. g. acidic ion exchangers or toluene sulfonic acid | Stripping gas or stripping gas + hexane |
| Benzyl amine | 70–71° C. at 10 torr | | |

Reactions of Carbonyl Compounds with Bases
Reactions of carboxylic acids with amines to form carboxylic acid amides Formation of the acid amide is favored by the continuous removal of water (substance to be separated) in the reaction stripper. The water-enriched auxiliary leaves the apparatus overhead, whereas the product is withdrawn at the bottom.

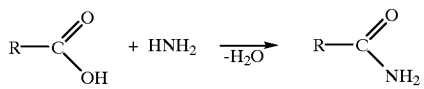

Example of a Substance

| Reactants | Boiling Point | Catalyst | Auxiliary |
|---|---|---|---|
| Capronic acid | 205° C. | Acids, e. g. acidic ion exchanger | Stripping gas or stripping gas + hexane |
| Dibutyl amine | 159–161° C. | | |

Guerbet Reaction

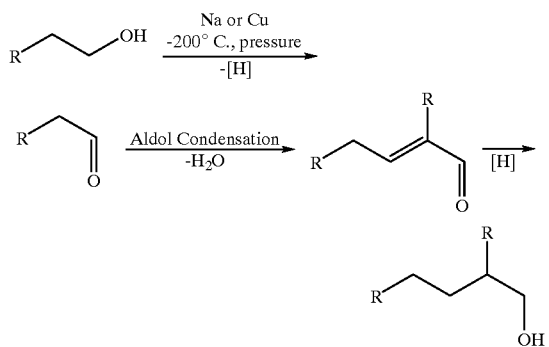

Esterification of Carboxylic Acids

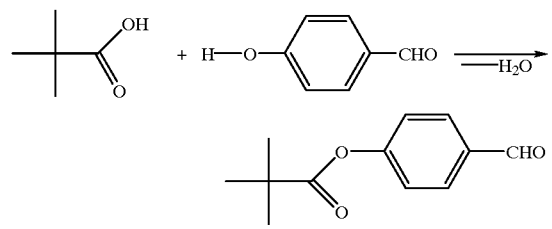

Example of a Substance

| Reactants | Catalyst | Auxiliary |
|---|---|---|
| Isobutanoic acid or pivalic acid with hydroxybenzaldehyde | Acids, e. g. acidic ion exchanger | Hydrogen as a stripping gas, optionally together with benzene, toluene, or, preferably, hexane |

Reactions of fatty acids with fatty alcohols to form fatty acid esters

It is an advantage of the process according to this invention that when using permanent gases as an auxiliary, ordinary coolers can be mounted into the condensers because the physical data of the permanent gases effecting the separation of substance are often very different from those of the substances to be separated (boiling point, heat of condensation, heat of evaporation). Thus, less energy is required for preheating because heat is only required for raising the temperature of the gas to reaction temperature, but not for heating a liquid entraining agent to effect vaporization.

Example of a Substance

| Reactants | Catalyst | Auxiliary |
|---|---|---|
| Fatty acid $C_6$—$C_{22}$, preferably $C_8$—$C_{22}$ Fatty alcohols $C_1$—$C_{22}$, preferably $C_8$—$C_{22}$ | Acids, e. g. acidic ion exchanger | Hydrogen or nitrogen as a stripping gas, optionally together with hexane (azeotrope former) |

Advantageous embodiment of this process (general, applicable to any reaction variant)

BRIEF DESCRIPTION OF THE DRAWING

A particularly advantageous embodiment of this process is shown in FIG. 1. A mixture of reactants is charged to the upper section of the reaction stripper. Chemical reaction takes place while the liquid reaction mixture, as a result of gravity, flows down via the stripper packing. The packing can be made of a solid or supported catalyst. Also suitable is an at least partially inert packing. The product obtained which is to be separated evaporates and is removed from the reaction zone by a stream of an auxiliary which is preferably charged countercurrently from the bottom. The auxiliary enriched with the substance to be separated leaves the reaction stripper overhead. After condensation of the substance to be separated, the auxiliary can be returned to the apparatus or, as a reactant, to a subsequent process stage. The desired liquid reaction product leaves the reaction stripper at the bottom.

When separating the water from reaction by means of an auxiliary, the reaction can be influenced to the advantage of the desired product, e.g. fatty acid ester. As shown in FIG. 1, a mixture consisting e.g. of fatty acid and fatty alcohol is charged to the upper section of the reaction stripper. Alternatively, the educts can partially be reacted by a preceding reaction which has the advantage of achieving the same conversion in a shorter reaction stripper column. In this case the product from the preceding reaction is charged to the reaction stripper.

Temperature and pressure of the reaction stripper are such that both the two reactants and the product, e.g. fatty acid ester, are liquid, while the component to be separated, e.g. water, evaporates and is mainly present in vaporous form.

The stripping gas, e.g. preheated, dry hydrogen, charged to the bottom of the apparatus flows to the top of the reaction stripper. While passing through the apparatus, it entrains the component to be separated, e.g. water. The hydrogen enriched with the component to be separated, e.g. water, leaves the apparatus overhead and reaches a condenser wherein it is separated from the component to be separated, e.g. water. Optionally, the hydrogen can be returned to the reaction stripper or may be employed in a different way. It is also possible to charge one of the reactants, preferably the alcohol, through a lateral inlet into the reaction stripper. This variant raises a further possibility of influencing the reaction to the advantage of the products. Furthermore, this process variant allows to control the temperature profile in the reaction stripper by preheating the side streams. It is a particular feature of the process according to this invention that the educts, e.g. carboxylic acid or, in the case of transesterification, the carboxylic acid ester, and the alcohol can advantageously be employed in equimolar quantities. If, however, overstoichiometric conversion is desired, the alcohol is charged in excess quantity. The product, e.g. the fatty acid ester, is removed from the lower section of the column.

The reaction stripper is provided with a solid catalyst. Thus, the reaction rate which is already accelerated by the stripping procedure can be further increased. When employing acidic catalysts, e.g. for an esterification process, it is expedient to use a solid acid as catalyst, e.g. an acidic ion exchanger. Ion exchangers which can also be employed at high reaction temperatures of up to 230° C. are particularly suitable. Water-sensitive catalysts, e.g. catalysts which adsorb the water from reaction, can be reactivated by drying after several cycles in order to increase conversion.

The process temperature is from 20 to 300° C., preferably 100 to 230° C. The process pressure is below atmospheric down to 50 bar, preferably 1.5 to 15 bar. It is surprising that during esterification a cross-sectional load of the liquid phase of <0.48 kg/m$^2$s has no perceptible effect on the fatty acid conversion, whereas at >0.48 kg/m$^2$s the conversion decreases, as is expected, as the cross-sectional load increases.

It is understood that any other reaction meeting the requirements described hereinabove can advantageously be carried out according to the novel process described herein. This process can be employed whenever the educts or products are higher-boiling, temperature-sensitive substances, e.g. in the production of intermediates for detergents, pharmaceuticals, and cosmetics. The reactions mentioned herein are only few examples of a large number of syntheses which can be performed employing the novel process presented herein.

Examples of Experiments

Experiments were carried out in a batch reactor in order to examine the kinetics of fatty acid esterification under stripping conditions. Furthermore, experiments were carried out in a lab-scale reaction stripper.

Batch Reactor Experiments

Fatty acid and fatty alcohol were charged to a batch reactor. The esterification reaction was carried out in the presence of a suitable catalyst. The acidic catalyst (ion exchanger) having the form of Raschig rings was arranged as a fixed bed in the reactor. The reaction volume of about 400 ml was filled with about 85 ml of solid catalyst. The liquid phase volume was about 230 ml. The remaining volume was the stripping gas volume. Nitrogen was employed as a stripping gas. This batch reactor simulates a section in a reaction stripper column.

The volume ratios of catalyst:liquid phase:gaseous phase chosen herein are not applicabe to a reaction stripper column. Despite the unfavorable parameter, i.e. the relatively low catalyst concentration in proportion to the liquid phase, the experiments proved that the process of this invention offers some advantages. Reaction temperature, feed ratio of the reactants, and volume of the stripping gas stream were varied in these experiments.

|                     | Fatty Acid Conversion [-] at Equimolar Feed Ratios | |
|---------------------|------------------|------------------------------|
| Reaction Time [min] | 0; 17; 60 I N$_2$/h | 120 I N$_2$/h (Volume of Stripping Gas Stream) |
| 20                  | ≈0.2             | 0.5                          |
| 40                  | ≈0.4             | 0.7                          |
| 75                  | ≈0.62            | 0.8                          |

It became apparent that the conversion of ester increases significantly with the reaction time if at the same time stripping gas is led through the batch reactor. This is achieved by the improved removal of the by-product water according to this invention by means of the stripping gas stream. The conversion increases as the stripping gas stream increases with time. The effect of simultaneous stripping in a batch reactor is not felt when employing very small stripping gas streams (<60 liters of nitrogen per hour). The experiments carried out in a batch reactor revealed that at a reaction temperature of 110° C. and atmospheric pressure the stripping gas stream (in this case nitrogen) should be greater than about 0.025 kg of nitrogen/(m$^2$s). The reference area is the cross-sectional area of the empty reaction stripper. The experiments were carried out in such a manner that the by-product to be eliminated, water, is obtained at a point above its boiling point. From process engineering aspects, this is the more advantageous variant of evaporation stripping.

In the second series of experiments the reaction temperature was 80° C. at atmospheric pressure. In these experiments water was obtained below its boiling point, i.e. as a liquid. In this case, too, it could be proved that the conversion increases by simultaneous stripping. However, the stripping efficiency was lower.

| Reaction Time [min] | Fatty Acid Conversion [-] at Equimolar Feed Ratios 129 I N$_2$/h (Volume of Stripping Gas Stream) |
|---------------------|------------------|
| 20                  | 0.07             |
| 40                  | 0.13             |
| 75                  | 0.25             |

Experiments in a Lab-Scale Reaction Stripper

A lab-scale reaction stripper was developed in order to prove the feasibility of the stripping process according to this invention in a column. The column had an internal diameter of 80 mm. For the first experiments a fixed catalyst bed consisting of acidic ion exchangers in the shape of Raschig rings was employed. The catalyst bed had a length of 1 m. The volume of the catalytic Raschig rings packing was about 5 liters. Equimolar quantities of fatty acid and fatty alcohol were charged to the top of the apparatus, while the stripping gas was fed counter-currently from the bottom. In the first experiments nitrogen was employed as a stripping gas.

| | |
|---|---|
| Cross-sectional load with liquid phase (fatty acid + alcohol) | 0.24 kg/(m$^2$s) |
| 1$^{st}$ cross-sectional load with nitrogen stripping gas | 0.049 kg/(m$^2$s) |
| 2$^{nd}$ cross-sectional load with nitrogen stripping gas | 0.085 kg/(m$^2$s) |
| 3$^{rd}$ cross-sectional load with stripping gas | 0 kg/(m$^2$s) |
| Reaction temperature | 110° C. |
| Reaction pressure | atmospheric |

Conversion of the fatty acid increased as the stripping gas stream increased (at least with small-volume to medium-volume streams).

Conversion [−] as a function of the volume of stripping gas stream after a reaction time of 90 minutes at $V_{I,ges} \approx 5.1$ l/h, T=110° C., and atmospheric pressure

| 0 | NI N$_2$/h | (3) | 0.15 |
|---|---|---|---|
| 1,500–2,000 | NI N$_2$/h | (2) | 0.27 |

It was also found that the water content in the products decreased as the stripping gas stream increased (at least with low-volume to medium-volume streams), i.e. the quality improved.

Water content after a reaction time of 85 minutes at $V_{I,ges}$26 5.1 l/h, T=110° C., and atmospheric pressure

| 0.25 wt. % H$_2$O | at 1,500–2,000 NI N$_2$/h | (2) |
|---|---|---|
| 0.39 wt. % H$_2$O | at 0 NI N$_2$/h | (3) |

Further experiments were carried out employing hydrogen as a stripping gas. The start-up behavior of the lab-scale reaction stripper was examined at two pressures. The pressures were chosen such that at a low pressure the water was obtained as a gas, while at a high pressure the water was obtained as a liquid. The other process parameters were:

| Cross-sectional load with liquid phase (= fatty acid + alcohol) | 0.48–0.54 kg/(m$^2$s) |
|---|---|
| 1$^{st}$ cross-sectional load with H$_2$ stripping gas at 2 bar | 3.15 · 10$^{-3}$ kg/(m$^2$s) |
| 2$^{nd}$ cross-sectional load with H$_2$ stripping gas at 0.35 bar | 1.42 · 10$^{-3}$ kg/(m$^2$s) |
| Reaction temperature | 110° C. |
| 1$^{st}$ reaction pressure | 2 bar above atmospheric |
| 2$^{nd}$ reaction pressure | 0.35 bar above atmospheric |

Like in the batch reactor experiments it became apparent that the stripping efficiency achieved by this evaporation stripping variant is higher than in a process wherein the water is obtained as a liquid.

Conversion [−] as a function of the volume of stripping gas stream after a reaction time of 90 minutes at $V_{I,ges} \approx 10$–11 l/h and T=110° C.

| 300 NI H$_2$/h at ≈2 bar pressure above atmospheric | (1) | 0.082 |
|---|---|---|
| 300 NI H$_2$/h at ≈0.35 bar pressure above atmospheric | (2) | 0.118 |

Furthermore, the residence time of liquid phase and liquid phase hold-up as a function of the volume of liquid phase stream was examined. When the liquid load in the reaction stripper was low, the hold-up was found to decrease, while the residence time increased. With low liquid loads the residence time of the liquid phase could be influenced significantly by the volume of the stripping gas stream. The reaction stripper ran smoothly even with wide variations of the liquid load (about 1:300 in the experiments). The volume of the stripping gas stream, too, could be varied in a very wide range, i.e. from 0 to about 1,000 l/h, without resulting in process stand-still for hydrodynamic reasons.

Further experiments for the esterification of fatty acids and fatty alcohols using an acidic ion exchanger (Amberlist) and hydrogen as a stripping gas were carried out in a pilot plant. The fatty alcohol was used in 10% excess. In order to determine the maximum conversion, several runs were performed at constant reaction parameters, the esterification product being returned to the process.

TABLE 1

Conversion per Run

| | Conversion [%] | | |
|---|---|---|---|
| Experiment No. | (1) | (2) | (3) |
| 1 | 53.6 | 62.3 | 62.3 |
| 2 | 76 | 87 | 81.9 |
| 3 | 89.8 | 90.6 | 89.6 |
| 4 | 94.4 | 90.9 | 92.8 |
| 5 | 96.6 | | 93.3 |

TABLE 2

Parameters (Volume of Stripping Gas Stream: 900 l H$_2$/h)

| Experiment No. | Pressure (above atmospheric) | Temperature |
|---|---|---|
| 1 | 0.35 bar | 140° C. |
| 2 | 0.5 bar | 160° C. |
| 3 | 3 bar | 180° C. |

What is claimed is:

1. A process carried out in a reaction column for the chemical reaction of substances, the reaction of which is affected by an unfavorable equilibrium position of the main reaction or a preceding equilibrium, wherein during the reaction one or more substances to be separated are continuously removed from the reaction mixture by one or more auxiliaries, characterized in that:

said chemical reaction of substances comprises a condensation reaction to produce a condensation product wherein through the reaction column a solid catalyst is arranged as a fixed bed;

a stripping gas which is a permanent gas or a mixture of permanent gases is led as an auxiliary; and temperature and pressure are adjusted such that in the reaction column all the educts are present as liquids or solutions of solids and the substance(s) to be separated is (are) predominantly gaseous/vaporous.

2. A process according to claim 1, characterized in that hydrogen is employed as a stripping gas.

3. A process according to any one of the preceding claims, characterized in that an entraining agent is additionally used in order to remove the substance to be separated.

4. A process according to claim 1, characterized in that the substance to be separated is additionally removed by employing a hydrocarbon as an entraining agent.

5. A process according to claim 1, characterized in that said condensation product to be separated has a molecular mass of less than 100 g/mole.

6. A process according to claim 5, characterized in that carboxylic acids are esterified with alcohols to form carboxylic acid esters.

7. A process according to claim 5, characterized in that carboxylic acid esters are transesterified with alcohols to form carboxylic acid esters.

8. A process according to claim 6, characterized in that $C_6$–$C_{22}$ carboxylic acids are esterified with $C_1$ to $C_{22}$ alcohols to form carboxylic acid esters.

9. A process according to claim 7, characterized in that carboxylic acid esters having a $C_6$–$C_{22}$ acid group and a $C_1$ to $C_4$ alcohol group are transesterified with $C_6$ to $C_{22}$ alcohols to form carboxylic acid esters.

10. A process according to claim 1, characterized in that an acidic solid catalyst is employed in the reaction column.

11. A process according to claim 1, characterized in that double bonds are simultaneously hydrogenated in the reaction column by using hydrogen as a permanent gas and catalysts known in the art.

12. A process according to claim 1, characterized in that a multifunctional catalyst is employed in the reaction column.

13. A process according to claim 1, characterized in that the stripping gas, optionally jointly with the entraining agent, is (are) contercurrently led through the reaction column from the bottom to the top, the substance to be separated is removed from the stripping gas and, optionally, the entraining agent in a condenser, and the stripping gas and, optionally, the entraining agent, or part thereof is (are) returned to the reaction column.

14. A process according to claim 1, characterized in that $C_8$–$C_{22}$ acids are esterified with $C_8$ to $C_{22}$ alcohols to form carboxylic acid esters.

15. A process according to claim 1, characterized in that carboxylic acid esters having a $C_8$–$C_{22}$ acid group and a $C_1$–$C_4$ alcohol group are transesterified with $C_8$ to $C_{22}$ alcohols to form carboxylic acid esters.

16. A process according to claim 12, characterized in that said multifunctional catalyst is of a type that can support an esterification reaction, a hydrogenation reaction, and/or an isomerization reaction.

* * * * *